(12) United States Patent
Tanaka et al.

(10) Patent No.: US 9,468,937 B2
(45) Date of Patent: Oct. 18, 2016

(54) AIR PURIFICATION DEVICE

(71) Applicant: DAIKIN INDUSTRIES, LTD., Osaka-shi, Osaka (JP)

(72) Inventors: Toshio Tanaka, Osaka (JP); Kenkichi Kagawa, Osaka (JP); Shunji Haruna, Osaka (JP); Tatsumi Enokida, Shiga (JP); Kei Suzumura, Shiga (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 14/428,324

(22) PCT Filed: Aug. 6, 2013

(86) PCT No.: PCT/JP2013/004751
§ 371 (c)(1),
(2) Date: Mar. 13, 2015

(87) PCT Pub. No.: WO2014/041737
PCT Pub. Date: Mar. 20, 2014

(65) Prior Publication Data
US 2015/0224516 A1    Aug. 13, 2015

(30) Foreign Application Priority Data

Sep. 14, 2012  (JP) ................................ 2012-203351

(51) Int. Cl.
*B03C 3/72* (2006.01)
*A61L 9/22* (2006.01)
(Continued)

(52) U.S. Cl.
CPC . *B03C 3/72* (2013.01); *A61L 9/22* (2013.01); *B03C 3/88* (2013.01); *F24F 3/166* (2013.01); *H01T 19/00* (2013.01); *H01T 23/00* (2013.01); *B03C 2201/24* (2013.01); *F24F 2003/1635* (2013.01)

(58) Field of Classification Search
CPC ....... A61L 9/22; B03C 2201/24; B03C 3/72; B03C 3/88; F24F 2003/1635; F24F 3/166; H01T 19/00; H01T 23/00
See application file for complete search history.

(56) References Cited

U.S. PATENT DOCUMENTS 4,892,271 A * 1/1990 Elford .................. B29C 59/103
156/272.6
2001/0030541 A1* 10/2001 Fujita ...................... H01T 19/00
324/455

(Continued)

FOREIGN PATENT DOCUMENTS

CN  1389008 A   1/2003
EP  1 980 317 A1  10/2008

(Continued)

OTHER PUBLICATIONS

International Search Report issued in PCT/JP2013/004751, dated Nov. 5, 2013.

*Primary Examiner* — Christopher P Jones
(74) *Attorney, Agent, or Firm* — Birch, Stewart, Kolasch & Birch, LLP (57) ABSTRACT

An air purification device includes a controller configured to perform a normal discharge operation in which a discharger generates streamer discharge to purify air, and an emergency discharge operation in which, in order to remove substances, which are components contained in air, adhering to electrodes of the discharger due to the normal discharge operation, a higher voltage than that in the normal discharge operation is applied to the electrodes to cause the discharger to generate spark discharge. The controller adjusts an application voltage such that a current value between the electrodes is maintained constant, and the upper limit V of the application voltage is set at a value greater than an inter-electrode distance of $d \times 1.2$ ($V \geq d \times 1.2$).

1 Claim, 5 Drawing Sheets

(51) Int. Cl.
  *F24F 3/16* (2006.01)
  *H01T 19/00* (2006.01)
  *H01T 23/00* (2006.01)
  *B03C 3/88* (2006.01)

(56) References Cited

U.S. PATENT DOCUMENTS

2003/0098650 A1  5/2003  Adachi et al.
2008/0314251 A1  12/2008  Tanaka et al.

FOREIGN PATENT DOCUMENTS

| JP | 2002-15834 A | 1/2002 |
| JP | 2004-335134 A | 11/2004 |
| JP | 2005-218748 A | 8/2005 |
| JP | 2006-15282 A | 1/2006 |
| JP | 2007-215985 A | 8/2007 |
| JP | 2011-104558 A | 6/2011 |
| JP | 2011-200369 A | 10/2011 |

* cited by examiner

AIR PURIFICATION DEVICE

TECHNICAL FIELD

The present invention relates to an air purification device configured to purify air by discharge.

BACKGROUND ART

As disclosed in, e.g., Patent Document 1, air purification devices configured to purify air by discharge have been conventionally known. The air purification device includes a discharge device with a pair of a discharge electrode and a counter electrode. In the discharge device, voltage is applied between the pair of electrodes to generate streamer discharge. In generating streamer discharge, high-reactive active species such as ozone and radicals are generated, and harmful components and odorous components contained in air are decomposed by the active species.

CITATION LIST

Patent Document

PATENT DOCUMENT Japanese Unexamined Patent Publication No. 2005-218748

SUMMARY OF THE INVENTION

Technical Problem

In the discharge device of the air purification device as described above, there is a disadvantage that a volatile silicon compound contained in air is oxidized into silica ($SiO_2$) by discharge, and then, the silica adheres to tip ends of the electrodes. Substances, such as silica, adhering to the electrode tip ends become resistance to block discharge. As a result, a disadvantage of lowering an air purification function arises.

The present invention has been made in view of the foregoing, and is intended to remove substances adhering, due to discharge, to electrodes generating, e.g., streamer discharge.

Solution to the Problem

A first aspect of the invention is intended for an air purification device including a discharger (50) having a pair of electrodes (51, 55) and being subjected to application of voltage between the electrodes (51, 55) to generate discharge. The air purification device of the first aspect of the invention includes a controller (60) configured to perform a normal discharge operation in which the discharger (50) generates corona discharge or streamer discharge to purify air, and an emergency discharge operation in which a higher voltage than that in the normal discharge operation is applied to the electrodes (51, 55) to cause the discharger (50) to generate spark discharge, thereby removing substances, which are components contained in air, adhering to the electrodes (51, 55) due to the normal discharge operation.

In the first aspect of the invention, the controller (60) causes the discharger (50) to perform the normal discharge operation and the emergency discharge operation. In the normal discharge operation, voltage is applied between the electrodes (51, 55) of the discharger (50) to generate corona discharge or streamer discharge, and then, high-reactive active species such as ozone and radicals are generated by such discharge. Harmful components and odorous components contained in air are decomposed by the active species, and therefore, the air is purified.

In the normal discharge operation described above, e.g., a volatile silicon compound contained in air is oxidized into, e.g., silica ($SiO_2$) by discharge, and then, adheres to the electrodes (51, 55). Thus, in the present invention, the emergency discharge operation is performed in the discharger (50). Since a higher voltage than that in the normal discharge operation is applied to the electrodes (51, 55) to generate spark discharge in the emergency discharge operation, substances adhering to the electrodes (51, 55) are removed by such spark discharge. As a result, the substances adhering to the electrodes (51, 55) are cleared.

A second aspect of the invention is intended for the air purification device of first aspect of the invention, in which the electrodes are a high-pressure electrode (51) having a projection (53) and being subjected to voltage application, and a planar ground electrode (55) facing the high-pressure electrode (51), and discharge is generated from a tip end of the projection (53) toward the ground electrode (55).

In the second aspect of the invention, in the normal discharge operation, e.g., silica adheres to a tip end of the projection (53) of the high-pressure electrode (51) serving as a discharge electrode. Since oxidizability by discharging is the highest at the tip end of the projection (53) of the high-pressure electrode (51), e.g., silica intensively adheres to the tip end of the projection (53). That is, the spots of the electrodes (51, 55) to which, lira adheres are limited to the tip end of the projection (53) of the high-pressure electrode (51). Moreover, the spot where spark discharge is generated in the emergency discharge operation is also the tip end of the projection (53) of the high-pressure electrode (51). Thus, it can be ensured that the substances adhering to the electrodes (51, 55) are effectively removed by spark discharge.

A third aspect of the invention is intended for the air purification device of the second aspect of the invention, in which an application voltage V (kV) to the high-pressure electrode (51) in the emergency discharge operation is a value satisfying $V \geq d \times 1.2$, where the distance between the electrodes (51, 55) is represented by d (mm).

In the case of using the projection electrode and the planar electrode as described above, the voltage at which spark discharge is generated is 1.1 to 1.2 kV/mm per unit distance between the electrodes (51, 55). In the third aspect of the invention, the application voltage V (kV) satisfies $V \geq d \times 1.2$, where the distance between the electrodes (51, 55) is represented by "d" (mm). Thus, it can be ensured that spark discharge is generated in the emerge discharge operation.

A fourth aspect of the invention is intended for the air purification device of the third aspect of the invention, in which the controller (60) adjusts the application voltage to the high-pressure electrode (51) such that the current value between the electrodes (51, 55) is maintained constant, and the upper limit of the application voltage is set at a value greater than the value satisfying $V \geq d \times 1.2$.

In the fourth aspect of the invention, the application voltage is adjusted such that the current between the electrodes (51, 55) is maintained at a constant value. That is, so-called constant current control is performed for the discharger (50). When, e.g., silica does not adhere to the projection (53) of the high-pressure electrode (51) in the normal discharge operation, a predetermined current value can be ensured with a relatively-low application voltage. The resistance between the electrodes (51, 55) increases as, e.g., silica adhering to the high-pressure electrode (51) increases in amount. Accordingly, the application voltage gradually increases in order to ensure the predetermined current value. When the application voltage increases to a predetermined value of V≥d×1.2, the emergency discharge operation is performed to generate spark discharge, thereby removing adhered substances such as silica. Moreover, since the upper limit of the application voltage is set at a greater value than a predetermined value of V≥d×1 it is ensured that the application voltage increases to the voltage value at which spark discharge is generated.

A fifth aspect of the invention is intended for the air purification device of the third aspect of the invention, in which the controller (60) increases the application voltage to the high-pressure electrode (51) to the value satisfying V≥d×1.2, thereby performing the emergency discharge operation.

In the fifth aspect of the invention, in the normal discharge operation, the emergency discharge operation is performed in such a manner that the application voltage is increased to a predetermined voltage of V≥d×1.2, at which spark discharge is generated, every lapse of a predetermined period of time, for example. In this case, if, e.g., silica adheres to the high-pressure electrode (51), such adhered substances are removed by spark discharge.

Advantages of the Invention

As described above, according to the present invention, the normal discharge operation for causing the discharger (50) to generate corona discharge or streamer discharge to purify air and the emergency discharge operation for applying, in order to remove substances, which are components contained in air, adhering to the electrodes (51, 55) due to the normal discharge operation, a higher voltage than that in the normal discharge operation to the electrodes (51, 55) to cause the discharger (50) to generate spark discharge are performed. Thus, since the emergency discharge operation is performed after the normal discharge operation is switched to the emergency discharge operation, the substances adhering to the electrodes (51, 55) in the normal discharge operation can be removed by spark discharge, and therefore, can be cleared. This allows a long-term normal discharge operation, and therefore, an air purification function by discharge can be maintained longer.

According to the second aspect of the invention, the pair of electrodes are the high-pressure electrode (51) including the projection (53) and being subjected to voltage application and the planar ground electrode (55) facing the high-pressure electrode (51), and discharge is generated from the tip end of the projection (53) toward the ground electrode (55). Thus adherence of e.g. silica and generation of spark discharge can occur at the same spot at each electrode (51, 55). Thus, it can be ensured that the substances adhering to the electrodes (51, 55) are effectively removed and cleared by spark discharge.

According to the third aspect of the invention, when the voltage at which spark discharge is generated is 1.1 to 1.2 kV/mm per unit distance between the electrodes (51, 55), the application voltage V (kV) is set at V≥d×1.2, where the distance between the electrodes (51, 55) is represented by "d" (mm). Thus, it can be ensured that spark discharge is generated in the emergency discharge operation.

According to the fourth aspect of the invention, the application voltage to the high-pressure electrode (51) is adjusted such that the current value between the electrodes (51, 55) is maintained constant, and the upper limit of the application voltage is set at a greater value than a predetermined value of V≥d×1.2. Thus, in the normal discharge operation, the application voltage can increase as, e.g., adhered silica increases in amount. When the application voltage increases to a predetermined value of V≥d×1.2, the emergency discharge operation is performed to remove adhered substances such as silica by spark discharge. As just described, according to the present invention, the emergency discharge operation can be performed at proper timing corresponding to the state of substance adherence. Thus, it can be ensured that adhered substances are removed without an additional unit configured to detect the state of substance adherence.

According to the fifth aspect of the invention, since the application voltage to the high-pressure electrode (51) is increased to a predetermined value of V≥d×1.2 to perform the emergency discharge operation, spark discharge can be generated only by control of the application voltage. Thus, it an be ensured that spark discharge is generated at desired timing of removing adhered substances to remove the adhered substances.

BRIEF DESCRIPTION OF THE DRAWINGS

FIGS. 3A and 3B are diagrams schematically illustrating the configuration of a discharger of the embodiment. FIG. 3A is viewed in the plane, and FIG. 3B is viewed from the side.

DESCRIPTION OF EMBODIMENTS

An embodiment of the present invention will be described below in detail with reference to drawings. Note that the embodiment described below will be set forth merely for the purpose of a preferred example in nature, and is not intended to limit the scope, applications, and use of the invention.

Figure 1:
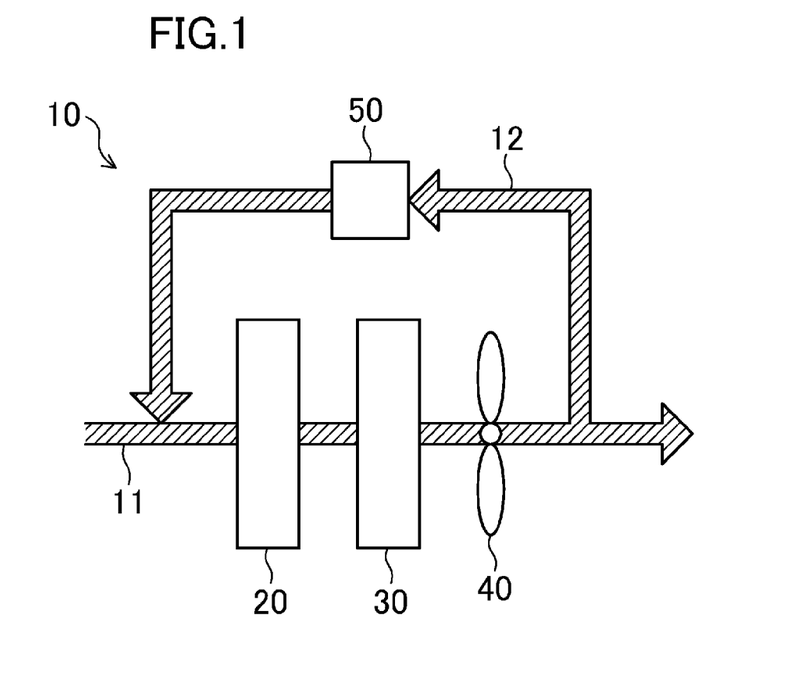
FIG. 1 is a schematic diagram illustrating the configuration of an air purification device of an embodiment.

Referring to FIG. 1, an air purification device (10) of the present embodiment includes a main passage (11) of air. A purifier (20), a humidifier (30), and a fan (40) are provided in this order from the upstream side toward the downstream side in the main passage (11). A return passage (12) of air branches downstream of the fan (40) in the main passage (11). The return passage (12) is connected to the upstream side of the purifier (20) in the main passage (11). Moreover, a discharger (50) is provided in the middle of the return passage (12). The main passage (11) and the return passage (12) form an air passage.

Figure 2:
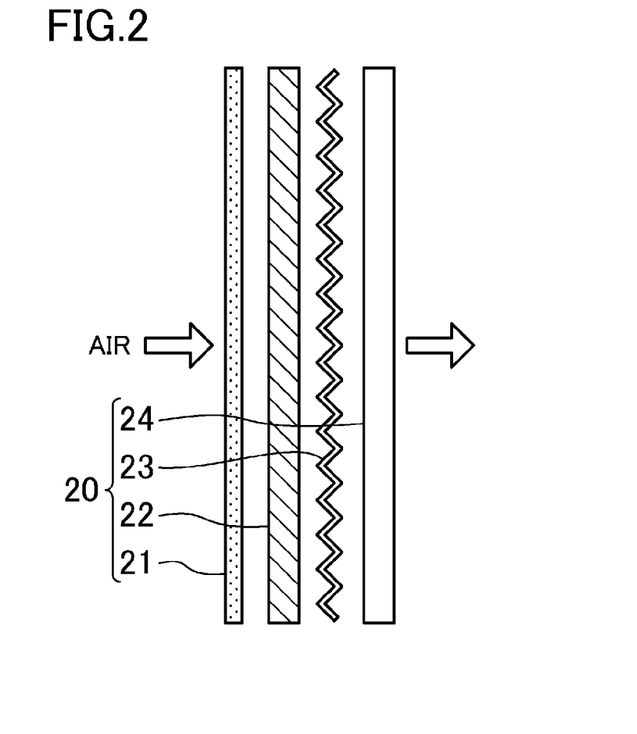
FIG. 2 is a schematic diagram illustrating the configuration of a purifier of the embodiment.

Referring to FIG. 2, the purifier (20) includes a pre-filter (21), an ionizer (22), a pleated filter (23), and a deodorizer member (24). The purifier (20) is configured to purify air.

The pre-filter (21) serves as a dust collection filter configured to physically trap relatively-large particles of dust contained in air in the main passage (11). The ionizer (22) serves as a dust charging unit configured to charge dust contained in air. The ionizer (22) is provided with, e.g., a linear electrode and a plate-shaped electrode facing the linear electrode. In the ionizer (22), voltage is applied from a power source to both electrodes, thereby generating corona discharge between the electrodes. Such corona discharge charges dust contained in air to a predetermined voltage (positive or negative charge). The pleated filter (23) is a corrugated plate-shaped electrostatic filter. That is, dust charged by the ionizer (22) is electrically attracted to the pleated filter (23), and then, is trapped by the pleated filter (23). Note that a deodorizing material such as a photocatalyst may be supported on the pleated filter (23). The deodorizer member (24) is configured such that a deodorant for deodorizing air is supported on a surface of a honeycomb base material. For example, an adsorbent for adsorbing treatment target components (odorous substances and harmful substances) contained in air or a catalyst for oxidatively decomposing the treatment target components may be used as the deodorant. In the present embodiment, these adsorbent and catalyst are capable of processing at least ozone as the treatment target components. That is, the purifier (20) of the present embodiment has the function of purifying air in the main passage (11) and the function of removing ozone.

Although not shown, the humidifier (30) includes a humidification rotor, a water tank, etc. The humidification rotor is supplied with moisture from the water tank. When air having passed through the deodorizer member (24) of the purifier (20) passes through the humidification rotor, moisture is provided from the humidification rotor to the air to humidify the air.

The fan (40) is configured to circulate air in the direction indicated by arrows illustrated in FIG. 1 in the main passage (11) and the return passage (12).

Figure 3A:
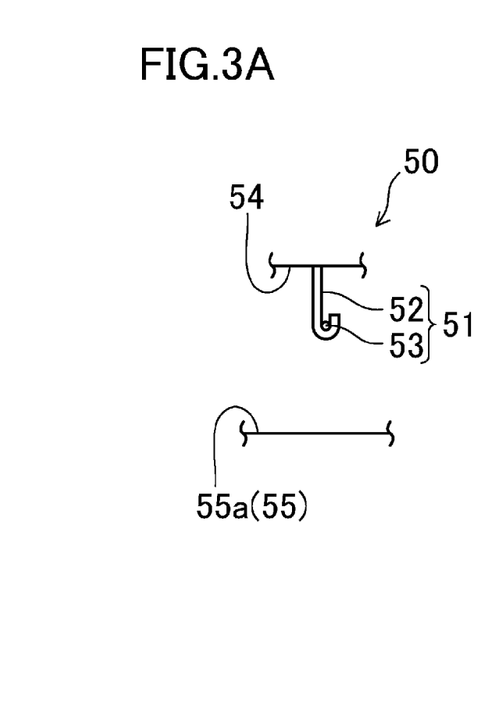
Figure 3B:
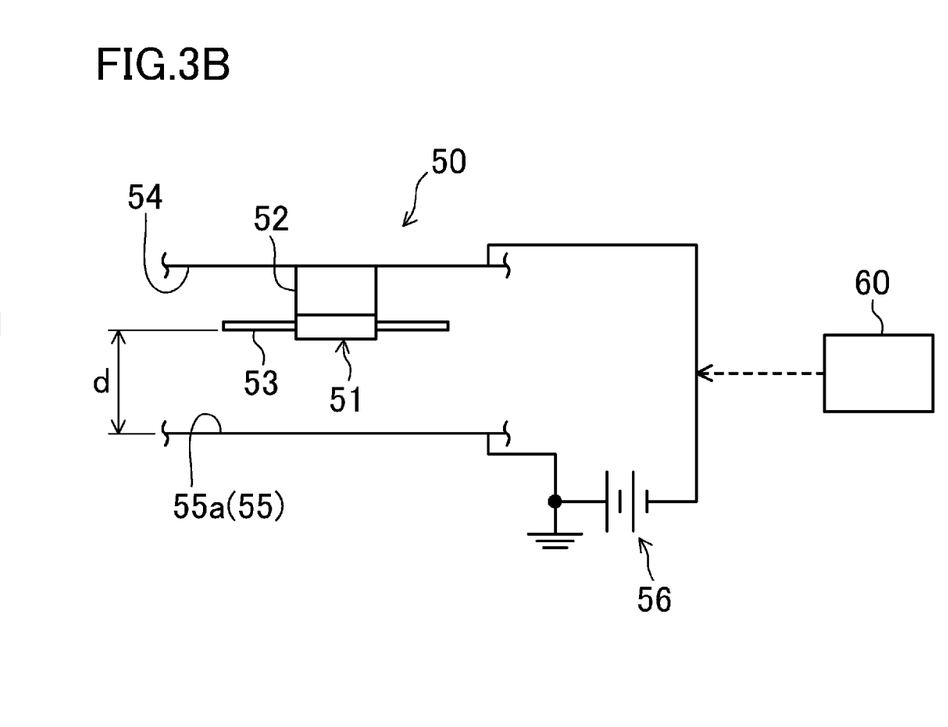

Referring to FIG. 3, the discharger (50) includes a discharge electrode (51), a counter electrode (55) facing the discharge electrode (51), and a power source (56). The discharge electrode (51) includes a fixed member (52) held by a holder member (54), and an electrode body (53) attached to the fixed member (52). The fixed member (52) is folded back at a tip end thereof, and the electrode body (53) is inserted into the folded-back part of the fixed member (52). The electrode body (53) is formed in a linear shape or a rod shape, and is inserted into the fixed member (52) in the state in which both ends of the electrode body (53) protrude from the fixed member (52). The protruding parts of the electrode body (53) from the fixed member (52) form projections of the discharge electrode (51) of the present invention. The counter electrode (55) has a front surface part (55a) formed in a planar shape. The electrode body (53) of the discharge electrode (51) is disposed substantially parallel to the front surface part (55a) of the counter electrode (55). That is, the protruding direction of the projections of the discharge electrode (51) is parallel to the front surface part (55a) of the counter electrode (55).

The discharge electrode (51) is a high-voltage electrode to which voltage is applied from the power source (56) through the holder member (54), and the counter electrode (55) is a ground electrode for which a ground is established. In the discharger (50), when voltage is applied to the discharge electrode (51), streamer discharge is generated from tip ends of the electrode body (53) toward the front surface part (55a) of the counter electrode (55). Streamer discharge is one type of plasma discharge, and high-reactive (high oxidative decomposability) active species (ozone, radicals, electrons, ions, etc.) are generated in generating discharge. In the discharger (50), harmful components and odorous components contained in air in the return passage (12) are decomposed by the active species generated by streamer discharge. As a result, air in the return passage (12) is purified. Air purified by the discharger (50) returns to the main passage (11).

Note that the discharger (50) may be configured to generate corona discharge instead of streamer discharge. Moreover, the discharge electrode (51) may be in such a form that the discharge electrode (51) has projections protruding from a plate-shaped substrate facing the counter electrode (55) toward the front surface part (55a) of the counter electrode (55). That is, the discharge electrode (51) may be in such a form that the protrusion direction of the projections of the discharge electrode (51) is substantially perpendicular to the front surface part (55a) of the counter electrode (55).

Referring to FIG. 3, the air purification device (10) further includes a controller (60) configured to control the discharger (50). The controller (60) is configured to perform a normal discharge operation for purifying air by streamer discharge generated by the discharger (50), and an emergency discharge operation for applying, in order to remove substances, i.e., components contained in air, adhering to the electrodes (51, 55) due to the normal discharge operation, a higher voltage than that in the normal discharge operation to the discharge electrode (51) to cause the discharger (50) to generate spark discharge. The detailed operation of the controller (60) will be described later.

<Operation>

The operation of the air purification device (10) will be described. Air sucked into the main passage (11) from a room flows into the purifier (20). In the purifier (20), relatively-large particles of dust contained in the air are trapped by the pre-filter (21). Dust etc. contained in the air having passed through the pre-filter (21) are charged by the ionizer (22). Then, when the air passes through the pleated filter (23), the dust etc. charged by the ionizer (22) adsorb to the pleated filter (23). The air having passed through the pleated filter (23) is deodorized when passing through the deodorizer member (24). The air having passed through the purifier (20) is humidified by the humidifier (30). Part of the air humidified by the humidifier (30) flows into the return passage (12), and the remaining air is discharged into the room. Harmful components etc. contained in the air having flowed into the ret passage (12) are decomposed by active species generated by the discharger (50), and the air is purified. The air purified by the discharger (50) returns to the main passage (11) again. After joining air sucked from the room, the air flows into the purifier (20).

<Operation of Discharger and Controller>

Figure 4:
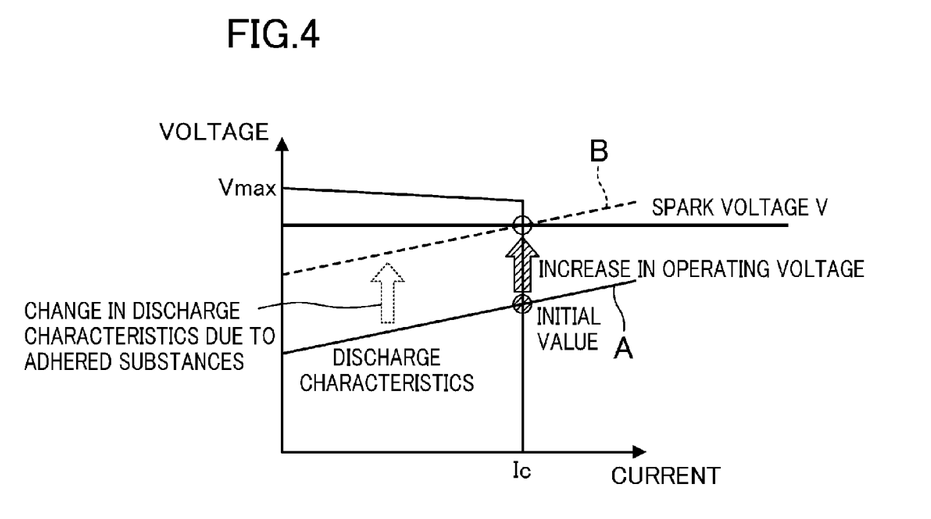
FIG. 4 is a graph showing the relationship between a voltage and a current in the discharger.

Referring to FIG. 4, the controller (60) performs so-called constant current control in which the voltage to be applied to the discharge electrode (51) is adjusted such that a current between the electrodes (51, 55) of the discharger (50) is a constant value in the discharger (50), the normal discharge operation and the emergency discharge operation can be performed by the controller (60).

In the normal discharge operation, voltage is applied to the discharge electrode (51) of the discharger (50) to generate earner discharge, and high-reactive active species are generated by such discharge. Harmful components and odorous components contained in air are decomposed by the active species, and as a result, the air is purified.

In the normal discharge operation, e.g., a volatile silicon compound contained in air is oxidized into, e.g., silica ($SiO_2$) by discharge, and then, adheres to the discharge electrode (51). Specifically, e.g., silica adheres to the tip ends of the electrode body (53) of the discharge electrode (51). The substances adhering to the discharge electrode (51)

become resistance to block discharge. In particular, silica is an insulating substance, and therefore, discharge blocking becomes more pronounced.

Thus, in the present embodiment, the emergency discharge operation is performed in the discharger (50). In the emergency discharge operation, a higher predetermined voltage than that in the normal discharge operation is applied to the discharge electrode (51), thereby generating spark discharge. Then, the substances adhering to the discharge electrode (51) are removed by spark discharge. As a result, the substances adhering to the electrodes (51, 55) are cleared. In the emergency discharge operation of the present embodiment, the predetermined voltage to be applied to the discharge electrode (51), i.e., the application voltage V (kV) (also referred to as a "spark voltage V") to the discharge electrode (51) generating spark discharge, is set at V≥d×1.2, where the distance between the electrodes (51, 55) is represented by "d" (mm). The distance d (mm) between the electrodes (51, 55) is illustrated in FIG. 3. Note that the distance d (mm) between the electrodes (51, 55) may be the distance from the center of the electrode body (53) to the front surface part (55a) of the counter electrode (55).

Figure 5:
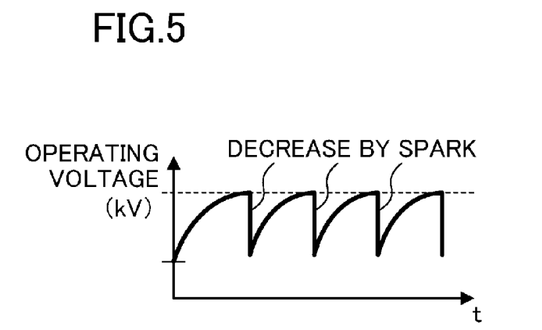
FIG. 5 is a graph showing the shift in operating voltage in the discharger.

Specifically, referring to FIG. 4, when, e.g., silica does not adhere to the electrode body (53) of the discharge electrode (51) in the normal discharge operation, the predetermined current value Ic can be ensured with a relatively-low application voltage. The resistance between the electrodes (51, 55) increases as, e.g., silica adhering to the discharge electrode (51) increases in amount. Accordingly, the characteristics of streamer discharge in the discharger (50) change. Then, the application voltage (operating voltage) gradually increases in order to ensure the predetermined current value Ic. When the application voltage increases to the spark voltage V (V≥d×1.2), the emergency discharge operation is performed to generate spark discharge, thereby removing adhered substances such as silica. When the substances adhering to the discharge electrode (51) are cleared in this manner, the operating voltage decreases, referring to FIG. 5, from the spark voltage V (voltage indicated by a dashed line in FIG. 5) to the operating voltage in the normal discharge operation. That is, since removal of the substances adhering to the discharge electrode (51) eliminates resistance, the emergency discharge operation is automatically switched to the normal discharge operation.

Figure 6:
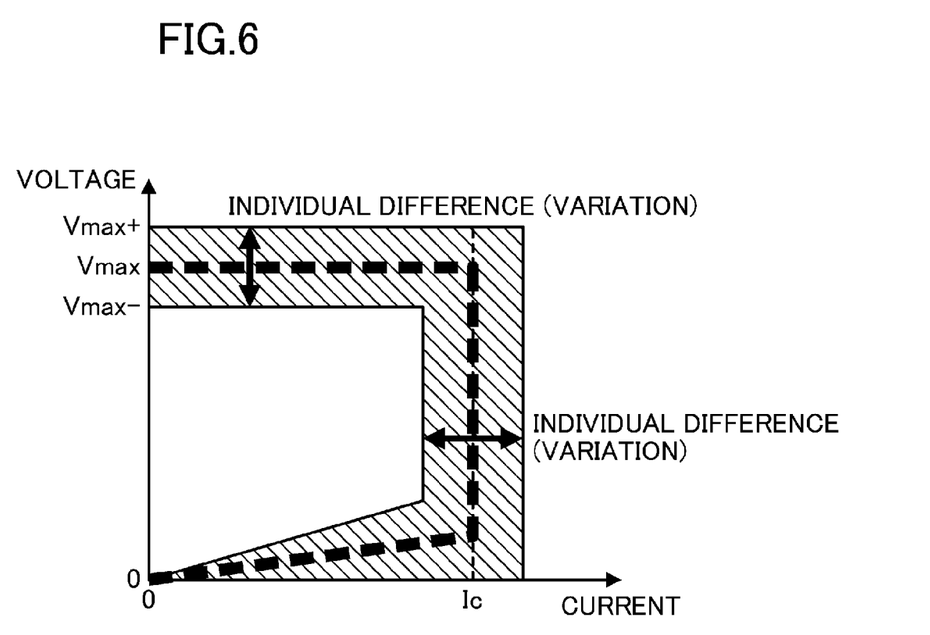
FIG. 6 is a graph showing the upper limit of voltage.

Referring to FIG. 4, in the power source (56), the upper limit Vmax of voltage (application voltage, operating voltage) is set at a value greater than the spark voltage V (V≥d×1.2). Thus, it is ensured that the operating voltage increases to the voltage value at which spark discharge is generated. Moreover, referring to FIG. 6, depending on products, there is an individual difference (variation) in upper limit Vmax of the power source (56) within a range of Vmax− to Vmax+. Thus, in the present embodiment, the value of Vmax− which is the lower limit of the upper limit Vmax is preferably set at equal to or greater than the spark voltage V (V≥d×1.2). Consequently, it can be ensured that the operating voltage increases, regardless of the individual difference depending on the power source (56), to the voltage value at which spark discharge is generated.

Advantages of Embodiment

According to the present embodiment, the normal discharge operation for causing the discharger (50) to generate streamer discharge (or corona discharge) to purify air and the emergency discharge operation for applying, in order to remove substances, i.e., components contained in air, adhering to the electrodes (51, 55) due to the normal discharge operation, a higher voltage than that in the normal discharge operation to the electrodes (51, 55) to cause the discharger (50) to generate spark discharge are performed. Thus, since the emergency discharge operation is performed after the normal discharge operation is switched to the emergency discharge operation, the substances adhering to the electrodes (51, 55) in the normal discharge operation can be removed by spark discharge, and therefore, can be cleared. This allows a long-term normal discharge operation, and therefore, an air purification function by discharge can be maintained longer.

According to the present embodiment, the pair of electrodes are the discharge electrode (51) including the electrode body (53) forming the projections and being subjected to voltage application d the planar counter electrode (55) facing the discharge electrode (51). Thus, adherence of, e.g., silica and generation of spark discharge occur at the same spot at each electrode (51, 55). That is, since oxidizability by discharging is the highest at the tip ends of the electrode body (53) forming the projections of the discharge electrode (51), e.g., silica intensively adheres to the tip ends of the electrode body (53). In other words, the spots of the electrodes (51, 55) to which, e.g., silica adheres are limited to the tip ends of the electrode body (53) of the discharge electrode (51). Moreover, the spots where spark discharge is generated in the emergency discharge operation are also the tip ends of the electrode body (53) of the discharge electrode (51). Thus, it can be ensured that the substances adhering to the electrodes (51, 55) are effectively removed and cleared by spark discharge.

When the voltage at which spark discharge is generated is 1.1 to 1.2 kV/mm per distance between the electrodes (51, 55), the application voltage V (kV) is, in the emergency discharge operation of the present embodiment, set at V≥d×1.2, where the distance between the electrodes (51, 55) is represented by "d" (mm). Thus, it can be ensured that spark discharge is generated in the emergency discharge operation.

According to the present embodiment, the application voltage (operating voltage) to the discharge electrode (51) is adjusted such that the current value between the electrodes (51, 55) is maintained constant, and the upper limit of the application voltage (operating voltage) is set at a greater c than a predetermined value of V≥d×1.2. Thus, in the normal discharge operation, the application voltage can increase as, e.g., adhered silica increases in amount. When the application voltage increases to a predetermined value of V≥d×1.2, the emergency discharge operation is performed to remove adhered substances such as silica by spark discharge. As just described, according to the present embodiment, the emergency discharge operation can be performed at proper timing corresponding to the state of substance adherence. Thus, it can be ensured that adhered substances are removed without an additional unit configured to detect the state of substance adherence.

Other Embodiments

The Foregoing Embodiment may have the Following Configurations.

Figure 7:
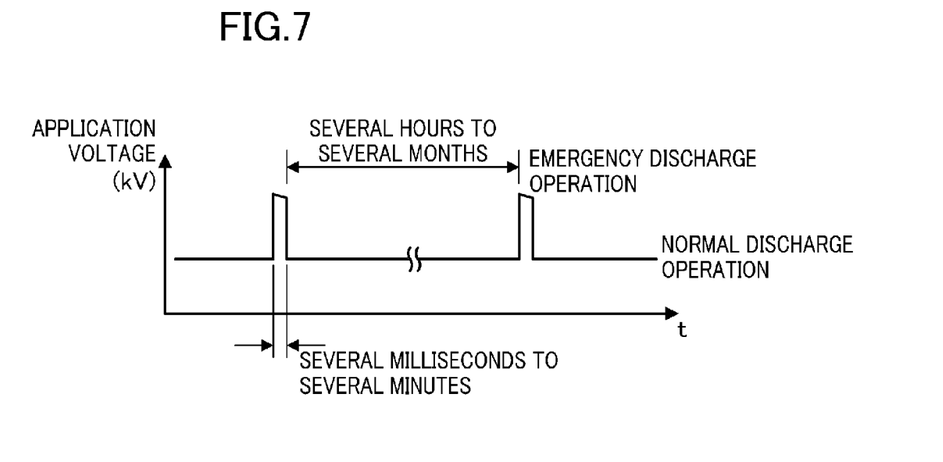
FIG. 7 is a time chart showing a normal discharge operation and an emergency discharge operation of another embodiment.

For example, the constant current control is performed for the discharger (50) in the foregoing embodiment, but the voltage control for controlling the voltage to be applied to the discharger (50) may be performed. In this case, referring to FIG. 7, the controller (60) may increase the application voltage to the discharge electrode (51) to the spark voltage V (V≥d×1.2) ever time the normal discharge operation is performed in the discharger (50) for a predetermined period of time (several hours to several months) to perform the emergency discharge operation for a predetermined period of time (several milliseconds to several seconds). In such a state, if, e.g., silica adheres to the discharge electrode (51), such adhered substances are removed by spark discharge. When the substances adhering to the discharge electrode (51) are cleared as just described, the application voltage temporarily decreases to zero, and then, is increased to the application voltage in the normal discharge operation. According to the present embodiment, since spark discharge can be generated only by control of the application voltage, it can be ensured that spark discharge is generated at desired timing of removing adhered substances to remove the adhered substances.

Figure 8:
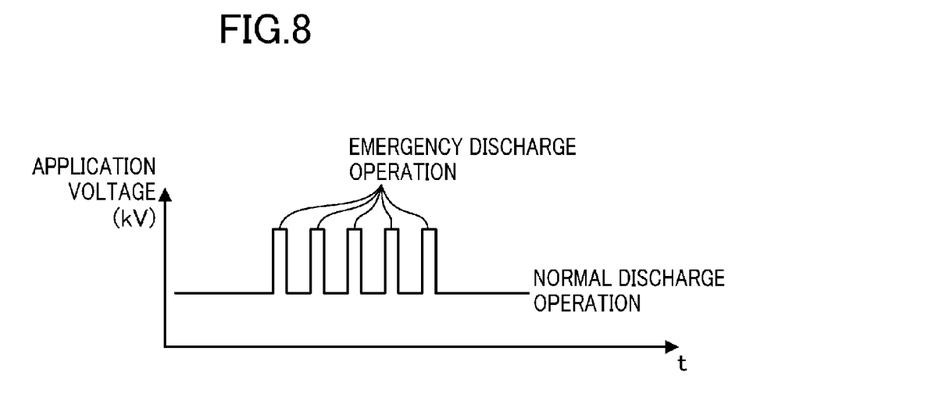
FIG. 8 is a time chart showing a normal discharge operation and an emergency discharge operation of still another embodiment.

Referring to FIG. 8, the emergency discharge operation may be intermittently performed more than once every time the normal discharge operation is performed for a predetermined period of time. That is, the operation of increasing the application voltage to the discharge eke ode (51) to the spark voltage V (V≥d×1.2) may be intermittently performed more than once every time the normal discharge operation is performed for the predetermined period of time. Spark discharge is not always generated right after the application voltage is increased to the spark voltage V. Harmful ozone and discharge sound are generated before spark discharge is generated and after the spark voltage V is applied. Thus, although spark discharge is not promptly generated, and generation of ozone etc. becomes more pronounced as the time till generation of spark discharge increases, the spark voltage V is intermittently applied more than once as described above, and therefore generation of ozone etc. can be reduced.

INDUSTRIAL APPLICABILITY

As described above, the present invention is useful for an a purification device including electrodes generating discharge.

DESCRIPTION OF REFERENCE CHARACTERS

10 Air Purification Device
50 Discharger
51 Discharge Electrode (High-Voltage Electrode)
53 Electrode Body (Projection)
55 Counter Electrode (Ground Electrode)
60 Controller

The invention claimed is:

1. An air purification device including a discharger having a pair of electrodes and being subjected to application of voltage between the electrodes to generate discharge, comprising:
a controller configured to perform
a normal discharge operation in which the discharger generates corona discharge or streamer discharge to purify air, and
an emergency discharge operation in which a higher voltage than that in the normal discharge operation is applied to the electrodes to cause the discharger to generate spark discharge, thereby removing a substance, which is a component contained in air, adhering to the electrodes due to the normal discharge operation, wherein
the electrodes are
a high-pressure electrode having a projection and being subjected to voltage application, and
a planar ground electrode facing the high-pressure electrode,
discharge is generated from a tip end of the projection toward the ground electrode, and
the controller is configured to adjust the application voltage to the high-pressure electrode such that a current value between the electrodes is maintained constant despite said substance adhering to said electrodes during the normal discharge operation, and is configured to set an upper limit of the application voltage to be a value greater than d×1.2, where d represents a distance between the electrodes in millimeters, such that switching between the normal discharge operation and the emergency discharge operation is automatically performed.

* * * * *